United States Patent
Matsushita (12) 
(10) Patent No.: US 6,458,116 B1
(45) Date of Patent: Oct. 1, 2002

(54) DISPOSABLE PANTS OF TRUNKS-TYPE AND PROCESS FOR MAKING THE SAME

(75) Inventor: Michiyo Matsushita, Kagawa (JP)

(73) Assignee: Uni-Charm Co., Ltd., Ehime (JP)

( * ) Notice: Subject to any disclaimer, the term of this patent is extended or adjusted under 35 U.S.C. 154(b) by 0 days.

(21) Appl. No.: 09/979,580

(22) PCT Filed: Mar. 15, 2001

(86) PCT No.: PCT/JP01/02058

§ 371 (c)(1),
(2), (4) Date: Mar. 5, 2002

(87) PCT Pub. No.: WO01/67900

PCT Pub. Date: Sep. 20, 2001

(30) Foreign Application Priority Data

Mar. 16, 2000 (JP) ........................................ 2000-073682

(51) Int. Cl.[7] ............................................... A61F 13/72
(52) U.S. Cl. ........................... 604/396; 2/400; 604/392; 604/393; 604/394; 604/395; 604/385.19; 604/348; 604/402
(58) Field of Search ................................ 604/317–348, 604/349, 350–355, 358–402, 396, 392, 393, 394, 395, 385.19, 385.01; 2/400–406

(56) References Cited

U.S. PATENT DOCUMENTS

| | | | |
|---|---|---|---|
| 4,555,245 A | * | 11/1985 | Armbruster ................. 604/396 |
| 4,938,757 A | * | 7/1990 | Van Gompel et al. ...... 604/396 |
| 5,291,617 A | * | 3/1994 | Moretz et al. .................. 2/400 |
| 5,435,014 A | * | 7/1995 | Moretz et al. .................. 2/403 |
| 6,264,644 B1 | * | 7/2001 | Igaue et al. ................. 604/389 |
| 6,293,936 B1 | * | 9/2001 | Otsubo ........................ 604/396 |
| 6,293,937 B2 | * | 9/2001 | Matsushita et al. ......... 604/396 |

* cited by examiner

Primary Examiner—Jeanette Chapman
(74) Attorney, Agent, or Firm—Baker & Daniels

(57) ABSTRACT

Pants that include a pair of outer sheets, and an inner sheet folded along a transverse center line, and disposed between lower parts of the respective outer sheets. Each of the outer sheets has upper and lower end portions extending in a transverse direction and front and rear side edge portions extending in a longitudinal direction while the inner sheet has lower end portions extending below the transverse center line in the transverse direction and a panel in the vicinity of the transverse center line. The inner surfaces of the respective outer sheets are bonded to each other in the vicinity of upper portions of the front and rear side edge portions thereof while the inner surfaces of the respective outer sheets are bonded to the inner surface of the inner sheet in the vicinity of lower portions of the front and rear side edge portions as well as in the vicinity of the front and rear side edge portions of the inner sheet.

8 Claims, 4 Drawing Sheets

DISPOSABLE PANTS OF TRUNKS-TYPE AND PROCESS FOR MAKING THE SAME

TECHNICAL FIELD

The present invention provides, in one aspect, disposable trunks-type pants designed so that a space surrounding the wearer's torso and thighs can be easily formed and thereby good feeling to wear the pants can be correspondingly ensured. In another aspect, the present invention provides a process for making such pants with a high productivity per unit hour.

BACKGROUND ART

Japanese Laid-Open Patent Application No. 1994-63072A discloses disposable pants trunks-type basically comprising separately prepared front and rear bodies. These front and rear bodies are provided in regions thereof defining a crotch region with a bonding line curving so as to be convex toward a waist line and the inner side of the crotch region is provided with a liquid-absorbent panel which is relatively long in back-and-forth direction of the pants. The pants disclosed therein is said to be advantageous in that body excretion can be effectively absorbed in the crotch region by the liquid-absorbent panel attached to this crotch region.

However, the pants disclosed in the above-cited Application comprises the front and rear bodies flatly placed upon each other, so the wearer's torso and thighs would forcibly form a space within the pants when the pants are worn. In addition, the liquid-absorbent panel which is relatively long in the back-and-forth direction and has a desired width dimension is horizontally attached to the inner surface of the crotch region. Consequently, transversely opposite side edge portions of the panel may be intensely pressed against the wearer's skin and deteriorate feeling to wear the pants as the panel is compressed between the wearer's thighs.

In view of these problems as have been described above, an object of this invention is to provide, in one aspect, disposable pants of trunks-type improved so that a space surrounding the wearer's torso and thighs can be easily formed and thereby good feeling to wear the pants can be correspondingly ensured and, in another aspect, is to provide a process for making such pants with an improved productivity per unit hour.

DISCLOSURE OF THE INVENTION

According to one aspect of this invention, trunks-type disposable pants are provided which have a waist-opening at upper part and a pair of leg-openings at lower part thereof wherein a peripheral edge portions of the waist-opening is elastically stretchable in a circumferential direction of the waist-opening.

According to this invention, the pants comprise a pair of outer sheets arranged in plane-symmetry relationship with each other and a single inner sheet folded along a transverse center line extending in back-and-forth direction of the pants so that its outer surface is put flat together and disposed between lower parts of the outer sheets, the outer sheets respectively have upper and lower end portions extending in parallel to the transverse center line of the inner sheet in the transverse direction and front and rear side edge portions extending in a longitudinal direction orthogonal to the transverse center line, and the inner sheet has lower end portions extending in the transverse direction below the transverse center line, front and rear side edge portions extending in the longitudinal direction and a liquid-absorbent panel bonded to an inner surface of the inner sheet and extending downward from the transverse center line toward the lower end portions, and the outer sheets respectively have their inner surfaces bonded to each other in the vicinity of upper portions of the front and rear side edge portions of the outer sheets while the inner sheet has its inner surface bonded to the inner surfaces of the outer sheets in the vicinity of lower portions of the front and rear side edge portions of the outer sheets as well as in the vicinity of the front and rear side edge portions of the inner sheet.

According to another embodiment of this invention, the outer sheets and/or the inner sheet are formed of a hydrophobic nonwoven fabric being elastically stretchable in the transverse direction and the longitudinal direction, at least in the transverse direction.

According to another aspect of this invention, a process for making a trunks-type disposable pants is provided which comprises the steps of:

(a) feeding forward in a longitudinal direction a single continuous inner sheet having transversely opposite side edge portions extending in parallel to each other in the longitudinal direction and an imaginary fold line extending in the longitudinal direction to bisect a dimension between the transversely opposite side edge portions and simultaneously attaching liquid-absorbent panels to an inner surface of the inner sheet in respective bonding regions defined on the inner surface of the inner sheet in the vicinity of the fold line at predetermined intervals in the longitudinal direction, (b) folding the inner sheet along the fold line so that outer surface of the inner sheet is placed upon itself, (c) feeding forward in the longitudinal direction a pair of outer sheets each having transversely opposite side edge portions, a first elastic member bonded with tension to this outer sheet in the vicinity of one of the transversely opposite side edge portions so as to extend in the longitudinal direction and an imaginary center line extending in the longitudinal direction to bisect a dimension between the transversely opposite side edge portions and placing the outer sheet upon the inner surface of the inner sheet with the fold line of the inner sheet put in coincidence with the center lines of the outer sheets and the side edge portion provided with the first elastic members laid in the vicinity of the transversely opposite side edge portions of the inner sheet, (d) bonding the inner surface of the inner sheet to the inner surfaces of the outer sheets in first bonding regions each extending in a transverse direction immediately in front and behind the associated panel in the longitudinal direction and bonding the inner surfaces of the outer sheets to each other in the first bonding regions with the first elastic members being maintained under tension, and (e) cutting the inner sheet and the outer sheets along each pair of adjacent cutting lines extending in the transverse direction immediately in front and behind the associated panel in the longitudinal direction with these sheets being maintained bonded together in the first bonding region.

According to an alternative embodiment of the process, the step (a) or the step (b) includes the steps of feeding forward in the longitudinal direction a pair of continuous liquid-resistant side sheets each having transversely opposite side edge portions extending in parallel to each other in the longitudinal direction, one on the transversely opposite side edge portions having a second elastic member bonded with tension thereto so as to extend in the longitudinal direction with the one of the transversely opposite side edge portions laid in the vicinity of the fold line of the inner sheet, bonding the other of the transversely opposite side edges to the inner surface of the inner sheet extending between the lower end portions of the inner sheet and the panel with the second elastic members being maintained under tension, and bonding the side sheets to the inner surface of the inner sheet in second bonding regions extending in the transverse direction immediately in front and behind the panel in said longitudinal direction, and wherein the step (e) includes a step of cutting the inner sheet, the outer sheets and the side sheets together along the cutting lines with these sheets being maintained bonded in the first bonding regions as well as in the second bonding regions.

PREFERRED EMBODIMENTS OF THE INVENTION

Details of disposable pants of trunks-type according to this invention and the method for making the same will be more fully understood from the description given hereunder with reference to the accompanying drawings.

Figure 1:
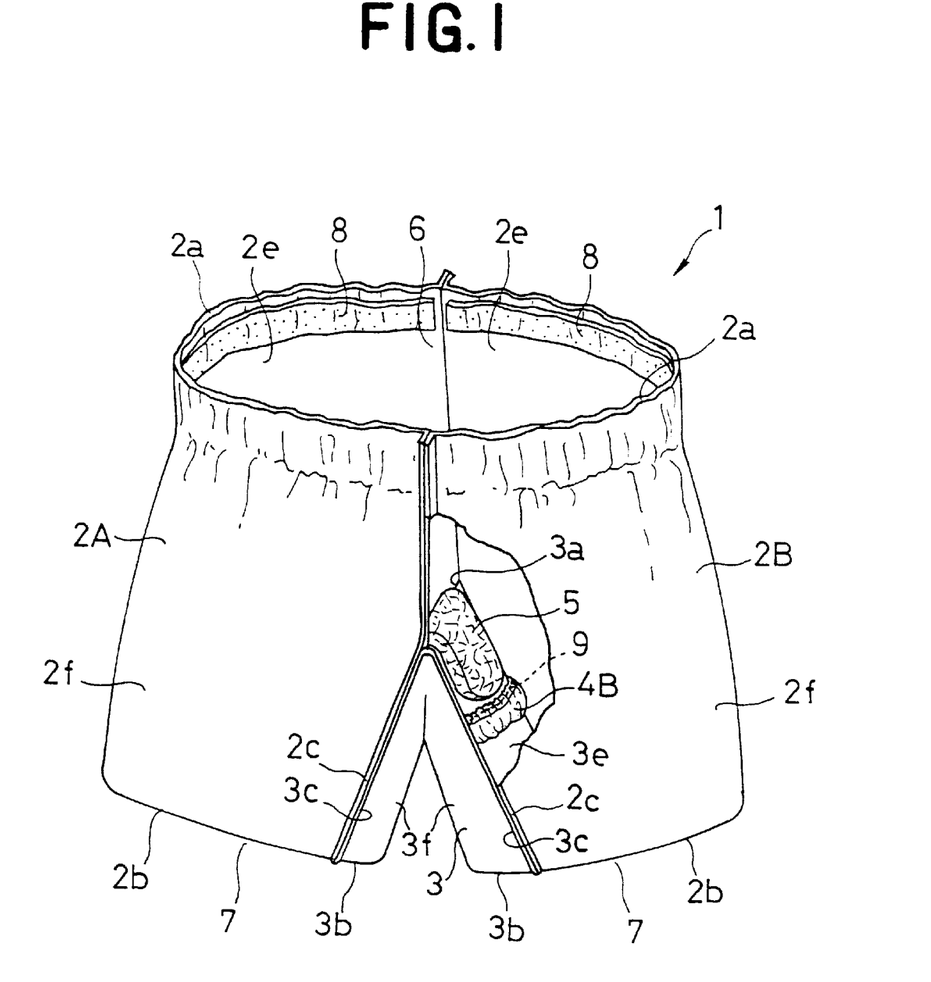
FIG. 1 is a perspective view showing disposable pants of trunks-type from the front.
Figure 2:
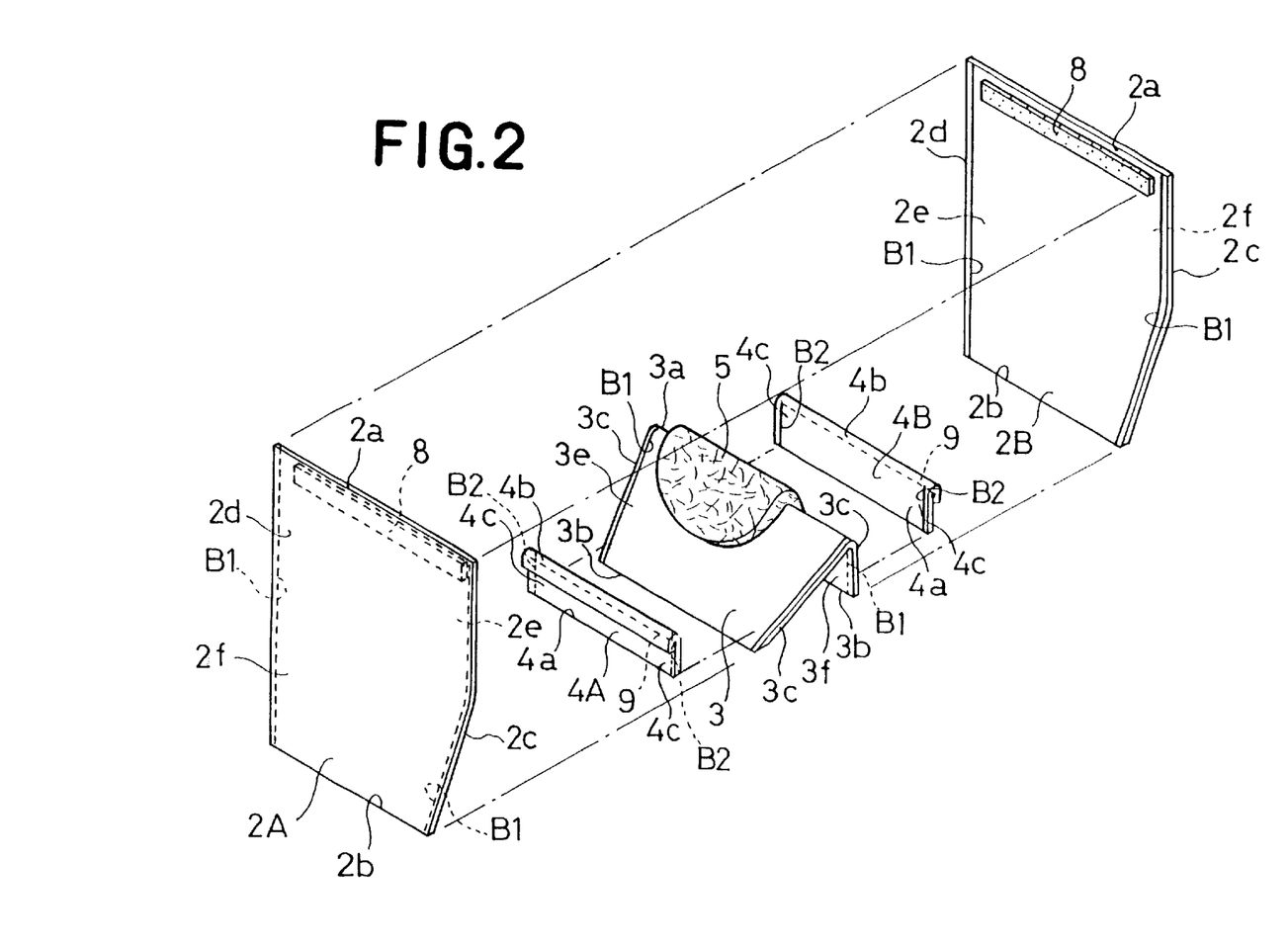
FIG. 2 is an exploded perspective view showing the pants shown by FIG. 1.

FIG. 1 is a perspective view showing disposable pants 1 as partially broken away and FIG. 2 is an exploded perspective view showing the pants 1 shown by FIG. 1. Referring to FIG. 2, outer sheets 2A, 2B are placed in a plane symmetry relationship to each other and an inner sheet 3 is placed between lower parts of these outer sheets 2A, 2B. Between the outer sheet 2A and the inner sheet 3 and between this inner sheet 3 and the outer sheet 2B, respective side sheets 4A, 4B are disposed, respectively. More specifically, the pants 1 comprise the pair of mutually symmetric outer sheets 2A, 2B, the single inner sheet 3, the pair of mutually symmetric liquid-resistant side sheets 4A, 4B and a liquid-absorbent panel 5.

In the pants, the outer sheets 2A, 2B define a waist-opening 6 at the upper part of the pants 1 while the outer sheets 2A, 2B and the inner sheet 3 define a pair of leg-openings 7 at the lower part of the pants 1. The waist-opening 6 is provided along its peripheral edge portion with film-like elastic members 8 extending together in a circumferential direction.

The outer sheets 2A, 2B respectively have upper and lower end portions 2a, 2b extending in parallel to each other in a transverse direction, and front and rear side edge portions 2c, 2d extending in parallel to each other in a longitudinal direction orthogonal to the transverse direction. The front and rear side edge portions 2c, 2d of the outer sheets 2A, 2B extend in the longitudinal direction so as to get nearer to each other as these side edge portions 2c, 2d extend from the upper ends 2a toward the lower end portions 2b. The outer sheets 2A, 2B are provided on respective inner surfaces 2e thereof opposed to each other with the elastic members 8 extending in the transverse direction in the vicinity of the respective upper ends 2a of the sheets 2A, 2B wherein these elastic members 8 are attached with tension to these sheets 2A, 2B so as to be associated with the waist-opening 6.

The inner sheet 3 is folded along its transverse center line 3a extending in a back and forth direction of the pants 1 so that the outer surface 3f of the inner sheet 3 may be put flat together. In this state, the inner sheet 3 has respective lower end portions 3b extending in parallel to each other in the transverse direction and front and rear side edge portions 3c, 3d extending in parallel to each other in the longitudinal direction. In this inner sheet 3, the front and rear side edge portions 3c, 3d extend so as to get nearer to each other as these side edge portions extend from the transverse center line 3a toward the lower end portions 3b. The panel 5 and the side sheets 4A, 4B extending in the transverse direction are attached to the inner surface 3e of the inner sheet 3. The panel 5 is provided in the form of a mat which is longer in the transverse direction and folded along the transverse center line 3a of the inner sheet 3 so as to extend from the transverse center line 3a toward the respective lower end portions 3b. The panel 5 is bonded to the inner surface 3e of the inner sheet 3 by means of adhesive (not shown).

Each of the side sheets 4A, 4B has a fixed side edge portion 4a extending in the transverse direction between the lower end portion 3b and the panel 5 and bonded to the inner surface 3e of the inner sheet 3, a free side edge portion 4b lying above the fixed side edge portion 4a and extending in parallel to the fixed side edge portion 4a in the transverse direction, and opposite fixed end portions 4c extending in parallel to the front and rear side edge portions 3c, 3d of the inner sheet 3 in the longitudinal direction and bonded to the inner sheet 3 in the vicinity of the front and rear side edge portions 3c, 3d thereof. An elastic member 9 extending in the transverse direction is attached with tension to the free side edge portion 4b so that this elastic member 9 may be covered with a part of the free side edge portion 4b.

The pants 1 may be assembled from the state as illustrated in the exploded perspective view of FIG. 2 in a manner as follows: First, the fixed side edge portions 4a of the respective side sheets 4A, 4B are bonded between the lower end portion 3b of the inner sheet 3 and the panel 5. Simultaneously, the fixed end portions 4c of the respective side sheets 4A, 4B are bonded to the inner sheet 3 in the velocity of its front and rear side edge portions 3c, 3d along second bonding zones B2 extending in the longitudinal direction while the elastic members 9 are maintained under tension.

Then, the inner surfaces 2e of the respective outer sheets 2A, 2B and the inner surface 3e of the inner sheet 3 are put flat together so that the lower end portions 2b as well as the front and rear side edge portions 2c, 2d of the outer sheets 2A. 2B may coincide with the lower end portion 3b as well as the front and rear side edge portions 3c, 3d of the inner sheet 3, respectively. With these sheets 2A, 2B, 3 having been put flat together, the inner surfaces 2e of the respective outer sheets 2A, 2B are bonded together along first bonding zones B1 extending in the longitudinal direction in the vicinity of upper portions of the front and rear side edge portions 2c, 2d while the elastic members 8 are maintained under tension. The inner sheets 2e of the respective outer sheets 2A, 2B are bonded to the inner surface 3e of the inner sheet 3 along the first bonding zones B1 extending in the longitudinal direction in the vicinity of lower portions of the front and rear side edge portions 2c, 2d as well as in the vicinity of the front and rear side edge portions 3c, 3d of the inner sheet 3. Bonding of these sheets 2A, 2B, 3, 4A, 4B may be performed either in continuous or intermittent manner.

Figure 3:
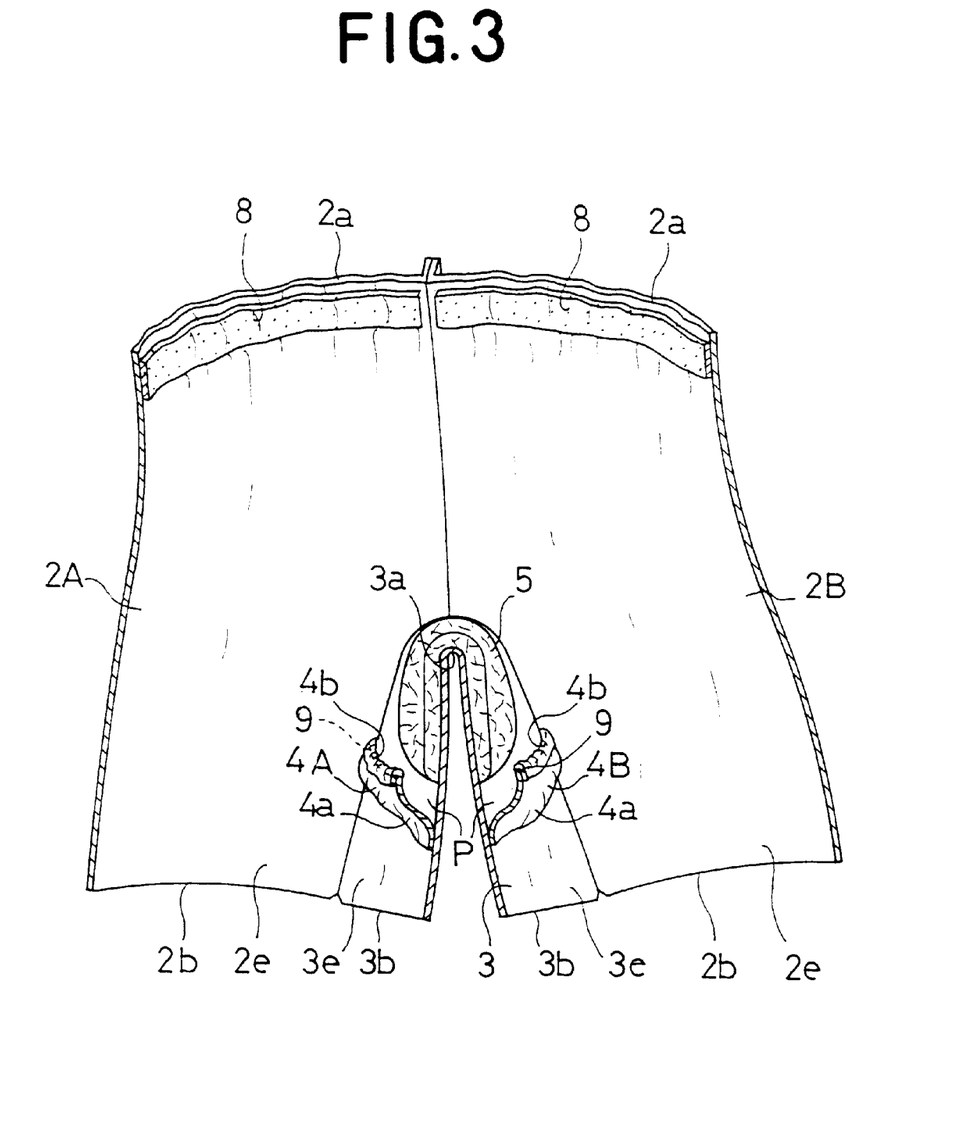
FIG. 3 is a perspective view showing the pants shown by FIG. 1 partially in a section taken along a line A—A.

FIG. 3 is a perspective view showing the pants 1 partially in a section taken along a line A—A in FIG. 1. The outer sheets 2A, 2B placed upon each other have the front and the rear side edge portions 2c, 2d thereof put flat together and extending outwardly of the pants 1. The outer sheets 2A, 2B and the inner sheet 3 placed upon one another also have the front and rear side edge portions 2c, 2d, 3c, 3d put flat together and extending outwardly of the pants 1.

In the pants 1, the inner surfaces 2e of the respective outer sheets 2A, 2B are bonded to each other along the first bonding zones B1 extending slightly inside the front and rear side edge portions 2c, 2d of these sheets 2A, 2B. Similarly, the inner surfaces 2e of the outer sheets 2A, 2B and the inner surface 3e of the inner sheet 3 are bonded to each other along the first bonding zones B1 extending slightly inside the front and rear side edge portions 2c, 2d, 3c, 3d of these sheets 2A, 2B, 3. With such a unique arrangement of the first bonding zones B1, stiffness of these bonding zones B1 is sufficiently alleviated by the front and rear side edge portions being free from bonding to reduce stimulation to the wearer's skin even when these front and rear side edge portions 2c, 2d, 3c, 3d of the sheets 2A, 2B, 3 come in contact with the wearer's skin.

In the pants 1, contraction of the elastic members 9 attached to the free side edge portions 4b of the respective side sheets 4A, 4B causes the free side edge portions 4b of the respective side sheets 4A, 4B to be opened transversely of the pants 1 and thereby causes the inner sheet 3 to cooperate with the side sheets 4A, 4B so as to define pockets P opening upwardly of the pants 1.

The pants 1 has a substantially cylindrical shape defined by the pair of outer sheets 2A, 2B and the inner sheet 3 lying in the wearer's crotch region and it is unnecessary for the pants 1 to forcibly define a space by the wearer's waist and thighs.

The panel 5 is not bulky in the crotch region since the panel 5 extends in parallel to the inner sheet 3 substantially in a longitudinal direction. Therefore, it is not likely that the feeling to wear the pants 1 might be deteriorated by the panel 5 as the panel 5 horizontally arranged in the crotch region is the case.

The outer sheets 2A, 2B and/or the inner sheet 3 and the side sheets 4A, 4B may be made from a hydrophobic nonwoven fabric. Such nonwoven fabric may be provided with apertures to improve its moisture-permeability or provided on its sheet surface with irregularities to improve its cushioning property. The inner sheet 3 to come in contact with the wearer's crotch region may be made from a highly moisture-permeable and flexible material such as a nonwoven fabric containing rayon or cotton fiber.

These sheets may be made from a composite nonwoven fabric (SMS nonwoven fabric) comprising a melt blown nonwoven fabric having a high water-resistance and two layers of spun bond nonwoven fabric being high in strength as well as in flexibility so that both sheet surfaces of the melt blown nonwoven fabric are sandwiched by sheet surfaces of the respective spun bond nonwoven fabric layers. The SMS composite nonwoven fabric is made by sandwiching the melt blown nonwoven fabric between the spun bond nonwoven fabric layers and then bonding the melt blown nonwoven fabric and the spun bond nonwoven fabric layers using the pressing technique. Use of the SMS nonwoven fabric advantageously enables the pants 1 to be high in strength as well as in water-resistance and to offer comfortable touch.

It is also possible to make the outer sheets 2A, 2B and/or the inner sheet 3 from a nonwoven fabric being stretchable at least in the longitudinal direction of these sheets 2A, 2B and/or inner sheet 3. When the stretchable nonwoven fabric is used as stock material for the outer sheets 2A, 2B, it is unnecessary to attach the elastic members 8 associated with the waist-opening to the outer sheets 2A, 2B in the vicinity of the upper edge portions 2a. When the stretchable nonwoven fabric is used as stock material for the inner sheet 3, the sheet well follows movement of the wearer's thighs and there is no anxiety that the sheet 3 might be distorted or turned over.

As stock material for the elastic members 8, 9, a stretchable film made of synthetic rubber, natural rubber, or material containing synthetic rubber, a spun bond nonwoven fabric or a melt blown nonwoven fabric containing synthetic rubber as principal ingredient or the other may be used. It is also possible to cover the elastic members 8, 9 with a nonwoven fabric and then to bond this assembly to another nonwoven fabric. 2f of the respective outer sheets 2A, 2B. Alternatively, it is also possible to attach the elastic members 8 associated with the waist-opening to the inner surfaces of the respective outer sheets 2A, 2B and to cover exposed zones of the elastic members associated with the waist-opening with nonwoven fabric so that these elastic members 8 might come in contact with the wearer's skin.

The liquid-absorbent panel 5 comprises a mixture of fluff pulp and super absorbent polymer particles compressed in a desired thickness and entirely covered with a liquid-pervious sheet (not shown) such as tissue paper.

Attachment of the elastic members 8, 9, and bonding of the sheets 2A, 2B, 3, 4A, 4B may be achieved using adhesive such as hot melt adhesive or pressure-sensitive adhesive or heat-welding technique such as heat-sealing or sonic-sealing.

Figure 4:
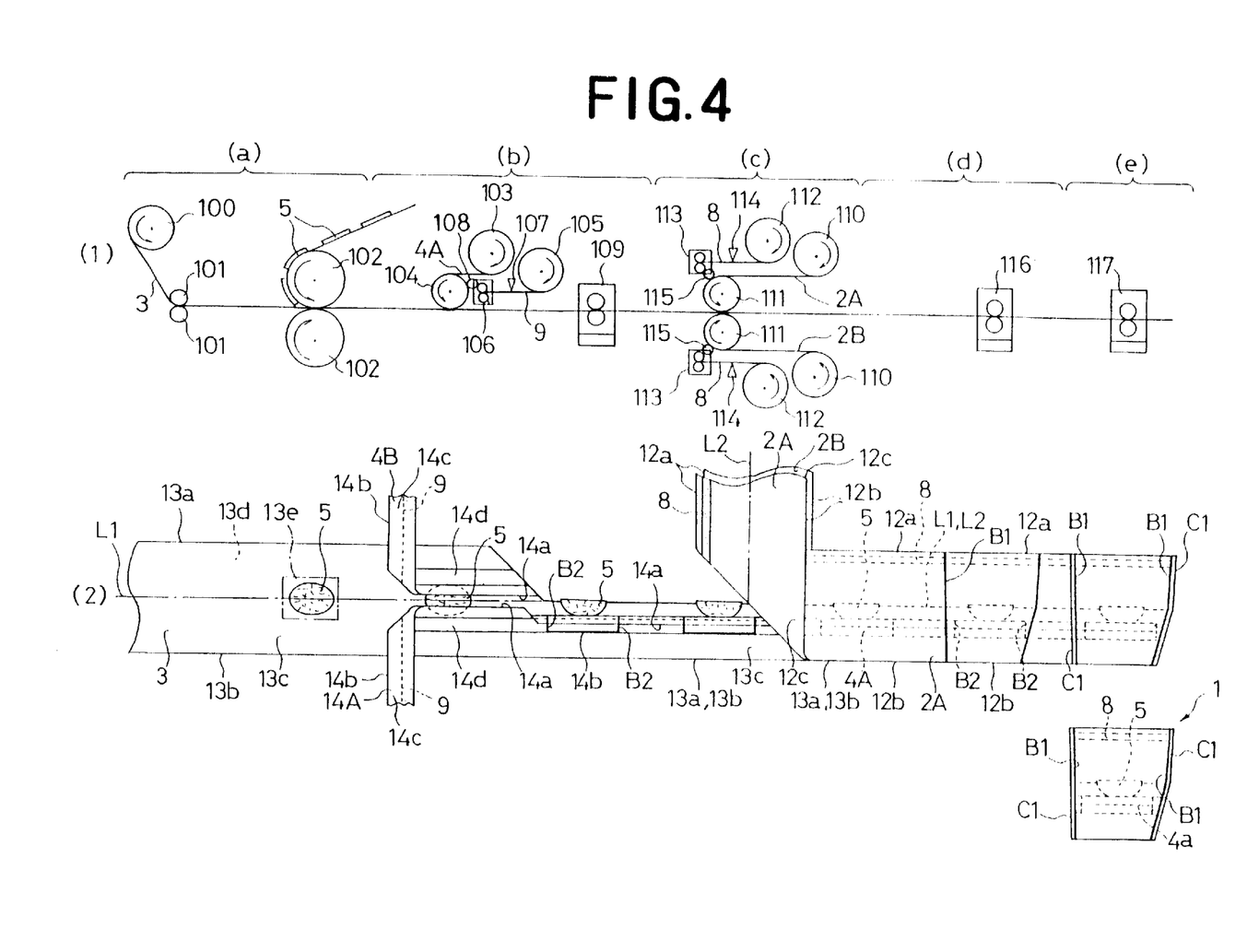
FIG. 4 is a diagram schematically illustrating a process for making the pants shown by FIG. 1.

FIG. 4 is a diagram schematically illustrating a process for making the pants 1 shown by FIG. 1, in which (1) illustrates the process in a side view and (2) illustrates the process in a plan view. As illustrated therein, the pants 1 can be made through a first step (a)—a fifth step (e) using the single continuous inner sheet 3, the pair of continuous outer sheets 2A, 2B, the pair of continuous liquid-resistant side sheets 4A, 4B and a plurality of mat-like liquid-absorbent panels 5.

The inner sheet 3 has transversely opposite side edges 13a, 13b extending in parallel to each other in the longitudinal direction and an imaginary fold line L1 extending in the longitudinal direction so as to bisect a dimension between the opposite side edges 13a, 13b.

Each of the outer sheets 2A, 2b has transversely opposite side edges 12a, 12b extending in parallel to each other in the longitudinal direction and an imaginary center line L2 extending in the longitudinal direction so as to bisect a dimension between the side edges 12a, 12b. The inner sheet 3 and the outer sheets 2A, 2B are substantially similar to each other so far as the width dimensions thereof are concerned.

Each of the side sheets 4A, 4B has transversely opposite side edges 14a, 14b extending in parallel to each other in the longitudinal direction so that a portion of the sheet 4A, 4B extending in the vicinity of the one side edge 14a is destined to define the free side edge portion 4b of each side sheet 4A, 4B shown in FIG. 1 and a portion of the sheet 4A, 4B extending in the vicinity of the other side edge 14b is destined to define the fixed side edge portion 4a.

These sheets 2A, 2B, 3, 4A, 4B are fed to and transported through the respective steps (a)–(e) appropriate means such as nip-rolls and suction drums rotated by suitable drive means. These sheets 2A, 2B, 3, 4A, 4B are fed to and transported through the respective steps (a)–(e) at a same speed.

The first step (a) is the step of feeding the inner sheet 3 forward in the longitudinal direction to attach the panel 5 to the inner surface 13c of the sheet 3.

In the first step (a), the inner sheet 3 is drawn out from a supply roll 100 by a pair of nip rolls provided downstream of the nip rolls 101 so as to be rotated in opposite directions and then introduced into a nip between a pair of suction drums 102 provided downstream of the nip rolls 101 so as to be rotated in opposite directions.

One of the suction drums 102 holds on its peripheral surface a plurality of the panels 5 at desired intervals in circumferential direction under the action of suitable suction means. These panels 5 move together with the peripheral surface of the drum 102 holding them as the drums 102 rotate. The surfaces of the respective panels 5 facing the inner surface 13c of the sheet 3 have previously been coated with adhesive by an adhesive coating mechanism (not shown) provided upstream of the suction drums 102. The panels 5 are successively fed onto the peripheral surface of the one suction drum 102.

On a contact surface of these drums 102, the panels 5 are successively bonded to the inner sheet 3 in its imaginary bonding regions 13e, respectively. The bonding regions 13e are defined on the inner surface 13c of the inner sheet 3 in the vicinity of the fold line L1 substantially at regular intervals in the longitudinal direction of the sheet 3.

The second step (b) is the step of bonding the side sheets 4A, 4B to the inner surface 13c of the inner sheet 3 and folding the inner sheet 3 with its outer surface 13d being placed upon itself.

In the second step (b), the side sheets 4A, 4B are drawn out from respective supply rolls 103 by nip-rolls 104 provided downstream of these supply rolls 103. Simultaneously, the second elastic members 9 are drawn out from supply rolls 105 by a transfer mechanism 106.

The second elastic members 9 are continuously or intermittently coated with adhesive (not shown) by an adhesive coating mechanism 107 provided between the supply rolls 105 and the transfer mechanism 106. The second elastic members 9 are stretched at a given ratio by a stretcher means associated with the transfer mechanism 106 and introduced onto a suction drum 108. The second elastic members 9 are maintained under tension by suitable suction means associated with the suction drum 108. On a contact surface between the roll 104 and the drum 108, the second elastic members 9 are bonded with tension to respective outer surfaces of the side sheets 4A, 4B moving together with the peripheral surface of the roll 104 in the vicinity of the one side edge 14a of each side sheet 4A, 4B.

The inner sheet 3 and the side sheets 4A, 4B having the second elastic members 9 bonded thereto, respectively, are introduced into a folding/bonding mechanism 109 provided downstream of the nip-rolls 104 in the state that the one side edge 14a of each side sheet 4A, 4B lies in the vicinity of the fold line L1 of the sheet 3 and the inner surface 13c of the inner sheet 3 is placed upon the inner surfaces 14c of the side sheets 4A, 4B.

In the folding/bonding mechanism 109, the side sheets 4A, 4B are folded back in the vicinity of the one side edge 14a of each side sheet 4A, 4B so that the outer surface 14d of the side sheets 4A, 4B may be placed upon itself and thereby cover the respective second elastic members 9.

Then, the side sheets 4A, 4b placed upon each other are continuously or intermittently bonded to each other in the vicinity of the one side edge 14a of each side sheet 4A, 4B.

The folding/bonding mechanism 109 functions to bond the portion of each side sheet 4A, 4B extending in the vicinity of its other side edge 14b opposite to its one side edge 14a to the inner surface 13c of the inner sheet 3 extending between the respective side edges 13a, 13b and the panel 5 with the second elastic members being maintained under tension. The folding/bonding mechanism 109 further functions to bond the inner surfaces 14c of the side sheets 4A, 4B to the inner surface 13c of the inner sheet 3 along the second bonding regions B2 extending in the longitudinal direction beyond the individual panel 5 and also in the transverse direction in the vicinity of the panel 5. Thereafter, the folding/bonding mechanism 109 functions to fold the inner sheet 3 along the fold line L1 with its outer surface 13d being placed upon itself. The sheet 3 folded in this manner has its transversely opposite side edges 13a, 13b put in coincidence with each other.

In the second step (b), the second elastic members 9 are bonded to the inner surfaces 14c of the respective side sheets 4A, 4B in the vicinity of the one side edge 14a of each side sheet 4A, 4B and portions of the side sheets 4A, 4B extending in the vicinity of the one side edge 14a of each side sheet 4A, 4B so that the inner surfaces 14c of the respective side sheets 4A, 4B may be placed upon themselves so as to cover the second elastic members 9.

The third step (c) is the step of feeding the outer sheets 2A, 2B forward in the longitudinal direction so as to place these outer sheets 2A, 2B upon the inner sheet 3.

In the third step (c), the outer sheets 2A, 2B are drawn out from respective supply rolls 110 by a pair of nip-rolls 111 provided downstream of these supply rolls 110 and rotated in opposite directions. Simultaneously, the first elastic members 8 are drawn out from respective supply rolls 112 by a transfer mechanism 113.

The first elastic members 8 are continuously or intermittently coated with adhesive (not shown) by an adhesive coating mechanism 114 provided between the supply rolls 112 and the transfer mechanism 113. The first elastic members 8 are stretched at a given ratio by a stretcher means associated with the transfer mechanism 113 and introduced into a nip between suction drums 115. The first elastic members 8 are maintained under tension by suitable suction means associated with the suction drums 115. On contact surfaces between the rolls 111 and the drums 115, respectively, the first elastic members 9 are bonded with tension to respective outer surfaces of the outer sheets 2A, 2B moving together with the peripheral surfaces of the rolls 104 in the vicinity of the one side edge 12d of each outer sheet 2A, 2B.

On a contact surface of the nip-rolls 111, the inner sheet 3 and the outer sheets 2A, 2B having the first elastic members 8 bonded thereto are placed upon each other with the inner surface 13c of the inner sheet 3 disposed between the inner surfaces 12c of the outer sheets 2A, 2B. With these sheets 2A, 2B, 3 placed one upon another in this manner, the fold line L1 of the inner sheet 3 coincides with the center line L2 of the outer sheets 2A, 2B while the side edges 12b opposite to the side edges 12a of the respective outer sheets 2A, 2B coincide with the transversely opposite side edges 13a, 13b of the inner sheet 3.

The fourth step (d) is the step of bonding the inner surface 13c of the inner sheet 3 to the inner surfaces 12c of the respective outer sheets 2A, 2B and bonding the inner surfaces 12c of the respective outer sheets 2A, 2B to each other.

The inner sheet 3 and the outer sheets 2A, 2B in this manner are introduced into a bonding mechanism 116 provided in this fourth step (d). In this bonding mechanism 116, the inner surface 13c of the inner sheet 3 is successively bonded to the inner surfaces 12c of the outer sheets 2A, 2B in the first bonding regions B1 each extending in the transverse direction immediately in front and behind the respective panels 5. Simultaneously, the inner surfaces 12c of the respective outer sheets 2A, 2B are bonded to each other in the first bonding regions B1 while the first elastic members 9 are maintained under tension. Each pair of the adjacent first bonding regions extend across the transversely opposite side edges 12a, 12b of the outer sheets 2A, 2B so as to get nearer to each other as these adjacent first bonding regions B1 extend from the side edge 12a toward the other side edge 12b of the outer sheets 2A, 2B. An alternative arrangement is also possible that the first bonding regions B1 extend in coincidence with the second bonding regions B2.

The fifth step (e) is the step of cutting the inner sheet 3, the outer sheets 2A, 2B and the side sheets 4A, 4B together along cutting lines C1.

The inner sheet 3 and the outer sheets 2A, 2B bonded together are introduced in a cutter mechanism 117 in which the inner sheet 3, the outer sheets 2A, 2B and the side sheets 4A, 4B are cut along the cutting lines C1 extending in the transverse direction immediately in front and behind the respective panels 5 while these sheets 2A, 2B, 3, 4A, 4B are kept bonded together in the respective first and second bonding regions B1, B2.

Each pair of the adjacent cutting lines C1 extend in parallel to the associated pair of the adjacent first bonding regions B1 immediately outside the respective first bonding regions B1 between the side edges 12a, 12b of the outer sheets 2A, 2B. An alternative arrangement is also possible that these cutting lines C1 extend in coincidence with the associated first bonding regions B1. In this way, the individual pants 1 are obtained upon completion of the fifth step (e).

The folding/bonding mechanism 109 provided in the second step (b) as well as the folding/bonding mechanism 116 provided in the fourth step (d) are adapted to bond the sheets 2A, 2B, 3, 4A, 4B together using hot melt adhesive or heat-welding technique such as heat-sealing or sonic-sealing. The cutter mechanism 117 provided in the fifth step (e) is adapted to cut the sheets 2A, 2B, 3, 4A, 4B using laser beam or supersonic wave.

It is possible to bond the side sheets 4A, 4B to the inner surface 13c of the inner sheet 3 not in the second step but in the first step. It should be understood that the side sheets 4A, 4B are not essential and may be optionally eliminated from the components constituting the pants 1.

The disposable pants of trunks-type according to this invention can be easily produced and meet the requirements for the non-reused, i.e., disposable pants particularly in view of simplified construction thereof. Specifically, the inner sheet and the outer sheets may be placed one upon another and the inner surfaces of them may be bonded together to form the pants.

In the embodiment of the-pants according to which the side sheets are bonded to the inner sheet, contraction of the elastic members attached to the respective side sheets causes the respective side sheets to be opened transversely of the pants and thereby causes the inner sheet to cooperate with the side sheets so as to define pockets opening upwardly of the pants. In the respective pockets, the side sheets form barriers adapted to prevent leak of excretion from occurring in the crotch region.

Being different from the flat pants obtained merely by placing a pair of sheets upon each other, the pants according to this invention has a substantially cylindrical shape defined by the pair of outer sheets covering the torso and most of the thighs of the wearer and the inner sheet lying in the wearer's crotch region. In this way, the pants are formed therein a space receiving the wearer's torso and thighs. The panel is not bulky in the crotch region since the panel extends in parallel to the inner sheet substantially in a longitudinal direction. Therefore, it is not likely that the feeling to wear the pants might be deteriorated by the panel as the panel horizontally arranged in the crotch region is the case.

The process according to this invention for making the disposable pants of trunks-type enables the respective steps to be automatically and continuously performed and thereby to improve productivity per unit hour because the process comprises limited number of steps, i.e., of placing the inner sheet, the outer sheets and the side sheets upon one another, bonding these sheets together and cutting these sheets having been placed upon and bonded to one another.

What is claimed is:

1. Disposable pants which comprise:
    a waist-opening at upper portion thereof, said waist-opening having peripheral edge portions that are elastically stretchable in a circumferential direction thereof;
    a pair of leg-openings at lower portion thereof;
    a pair of outer sheets arranged in plane-symmetry relationship with each other; and
    a single inner sheet folded along a transverse center line extending along a front and rear direction of said pants so that an outer surface of said inner sheet is put flat together and disposed between lower portions of said outer sheets,
    said outer sheets having upper and lower end portions extending in parallel to the transverse center line of said inner sheet in a transverse direction and front and rear side edge portions extending in a longitudinal direction orthogonal to said transverse center line,
    said inner sheet having lower end portions extending in said transverse direction below said transverse center line, front and rear side edge portions extending in said longitudinal direction and a liquid-absorbent panel bonded to an inner surface of said inner sheet and extending downward from said transverse center line toward said lower end portions, and
    said outer sheets having inner surfaces that are bonded to each other in a vicinity of upper portions of said front and rear side edge portions of said outer sheets and the inner surface of said inner sheet being bonded to the inner surfaces of said outer sheets in the vicinity of lower portions of said front and rear side edge portions of said outer sheets and bonded in a vicinity of the front and rear side edge portions of said inner sheet.

2. The pants according to claim 1 further comprising a pair of liquid-resistant side sheets formed from nonwoven fabric and extending in the transverse direction, said liquid-resistant side sheets having fixed side edge portions bonded to said inner sheet between lower end portions thereof and said the liquid-absorbent panel so as to extend in said transverse direction, a free side edge portion of said liquid-resistant side sheets lying above said fixed side edge portion so as to extend in said transverse direction and fixed end portions of said liquid-resistant side sheets being bonded to said inner sheet in a vicinity of the front and rear side edge portions so as to extend in said longitudinal direction, free side edge portions of said liquid-resistant side sheets being provided with elastic members bonded under tension thereto so as to extend in said transverse direction.

3. The pants according to claim 1, wherein at least one of said outer sheets and said inner sheet are formed of a hydrophobic nonwoven fabric that is elastically stretchable in at least said transverse direction.

4. A process for making disposable pants which comprises the steps of:

(a) feeding a single continuous inner sheet along a first direction, said inner sheet having transversely opposite side edge portions extending in parallel to each other in said first direction and a fold line extending in said first direction, which fold line bisects a dimension between said transversely opposite side edge portions, and simultaneously attaching liquid-absorbent panels to an inner surface of said inner sheet in respective bonding regions defined on the inner surface of said inner sheet in the vicinity of said fold line at desired intervals in said first direction, (b) folding said inner sheet along said fold line so that an outer surface of said inner sheet is placed upon itself, (c) feeding a pair of outer sheets along said first direction, each of said outer sheets having transversely opposite side edge portions, a first elastic member bonded under tension to the outer sheets in a vicinity of one of said transversely opposite side edge portions so as to extend in said first direction and a center line extending in said first direction which bisects a dimension between said transversely opposite side edge portions, (d) placing said outer sheets upon the inner surface of said inner sheet with the fold line of said inner sheet aligned with the center lines of said outer sheets and the side edge portions of said outer sheets opposed to said side edge portions provided with the first elastic members laid in a vicinity of the transversely opposite side edge portions of said inner sheet, (e) bonding the inner surface of said inner sheet to the inner surfaces of said outer sheets in first bonding regions that extend in a second direction immediately in front and behind an attached liquid-absorbent panel in said first direction and bonding the inner surfaces of said outer sheets to each other in said first bonding regions with said first elastic members being maintained under tension, and (f) cutting said inner sheet and said outer sheets along pairs of adjacent cutting lines extend along the second direction immediately in front and behind an attached panel in said first direction with the inner and outer sheets being maintained bonded together in said first bonding region.

5. The process according to claim 4, wherein at least one of said step (a) or said step (b) includes the additional steps of:

(i) feeding a pair of continuous liquid-resistant side sheets along said first direction, each of said side sheets having transversely opposite side edge portions extending in parallel to each other along said first direction, one of said transversely opposite side edge portions of each of said side sheets having a second elastic member bonded under tension thereto so as to extend in said first direction with said one of said transversely opposite side edge portions laid in a vicinity of the fold line of said inner sheet, (ii) bonding said transversely opposite side edges of each of said side sheets which are opposed to the opposite side edges having the second elastic members to the inner surface of said inner sheet between the lower end portions of said inner sheet and said attached panel with said second elastic members being maintained under tension, and (iii) bonding said side sheets to the inner surface of said inner sheet in second bonding regions that extend in the second direction immediately in front and behind said attached panel in said first direction, and wherein said step (f) includes a step of cutting said inner sheet, said outer sheets and said side sheets along said cutting lines with these sheets being maintained bonded in said first bonding regions as well as in said second bonding regions.

6. The pants according to claim 2, wherein at least one of said outer sheets and said inner sheet are formed of a hydrophobic nonwoven fabric that is elastically stretchable in at least said transverse direction.

7. The pants according to claim 3, wherein at least one of said outer sheets and said inner sheet are formed of a hydrophobic nonwoven fabric that is elastically stretchable in both said transverse direction and the longitudinal direction.

8. The pants according to claim 6, wherein at least one of said outer sheets and said inner sheet are formed of a hydrophobic nonwoven fabric that is elastically stretchable in both said transverse direction and the longitudinal direction.

* * * * *